United States Patent [19]

Heuillon

[11] Patent Number: 5,254,103

[45] Date of Patent: Oct. 19, 1993

[54] DENTAL SYRINGE WITH DISPOSABLE PROTECTIVE TUBING

[76] Inventor: Melle A. Heuillon, 3 rue Petite Rue, 55170 Ancerville, France

[21] Appl. No.: 703,609

[22] Filed: May 21, 1991

[51] Int. Cl.$^5$ ............................................. B61M 5/00
[52] U.S. Cl. ............................ 604/263; 128/200.14
[58] Field of Search ................. 433/80; 200/14; 604/263, 264, 268, 181, 192, 199; 128/200.14-200.23

[56] References Cited

U.S. PATENT DOCUMENTS

| | | | |
|---|---|---|---|
| 911,646 | 2/1909 | Cook et al. | 128/200.14 |
| 2,299,710 | 10/1942 | Dray | 128/200.14 |
| 4,859,182 | 8/1989 | Nerli | 433/80 |

Primary Examiner—C. Fred Rosenbaum
Assistant Examiner—Manuel Mendez
Attorney, Agent, or Firm—Weiser & Associates

[57] ABSTRACT

A dental syringe for projecting air, water or a mixture of air and water in dental surgery, and a detachable and disposable tube for preventing microbial and viral contamination between patients, are interconnected by a nozzle which includes an adapter at a proximal end of the nozzle having a connector for engaging the syringe, a male conical projection at a distal end of the nozzle for receiving the tube, and longitudinal passages for discharging air and water from the end of the syringe.

10 Claims, 1 Drawing Sheet

DENTAL SYRINGE WITH DISPOSABLE PROTECTIVE TUBING

BACKGROUND OF THE INVENTION

The present invention generally relates to dental syringes for projecting air, water or mixtures of air and water in dental surgery, and more particularly, to dental syringes adapted to receive detachable and disposable means for preventing microbial or viral (or both) contamination between patients.

As recognized in this art field, a "dental syringe" is an apparatus used by dentists to pulverize bone employing a high pressure fluid directed onto a dental zone to be treated. The "fluid" can include air, water or mixtures of air and water, as desired.

Devices of this general type are known, one example being the device which is disclosed in U.S. Pat. No. 4,907,968. In these devices, temporary protective shields are provided for the nozzle of the dental syringe. However, the resulting fit is often imperfect, and removal of the protective sleeve can be relatively laborious. Moreover, the various different types of syringe nozzles which presently exist require a corresponding number of different shields, making the use of such devices of little commercial interest.

SUMMARY OF THE INVENTION

It is therefore the principal object of the present invention to provide a dental syringe with a protective shield which is not subject to the foregoing limitations.

These and other objects which will be apparent are achieved in accordance with the present invention by providing a dental syringe for projecting air, water or mixtures of air and water in dental surgery, with a removable and disposable tubular enclosure for preventing microbial or viral (or both) contamination between patients, making use of a nozzle which includes an adapter at a proximal end of the nozzle having a connector for engaging the syringe, a male conical structure at a distal end of the nozzle for receiving a disposable tubing member (by an interlocking engagement, a fitting, or a screw connection), and longitudinal passages for discharging air and water from the end of the syringe.

Resulting from this, the disposable tubing member is made usable with any type of dental syringe. It suffices to provide a series of adapters which are standardized at their proximal connection in order to equip the majority of those dental syringes which are currently on the market. Preferably, the nozzle is threaded so that the tubing member can be mounted to the conical end through a self-tapping arrangement. Desirably, the nozzle will include the different passages which are needed for introducing and for distributing the fluids to be discharged toward the extremity of the syringe nozzle.

For further detail regarding a preferred embodiment syringe nozzle incorporating the improvements of the present invention, reference is made to the detailed description which is provided below, together with the following drawings.

DETAILED DESCRIPTION OF PREFERRED EMBODIMENTS

Figure 1:
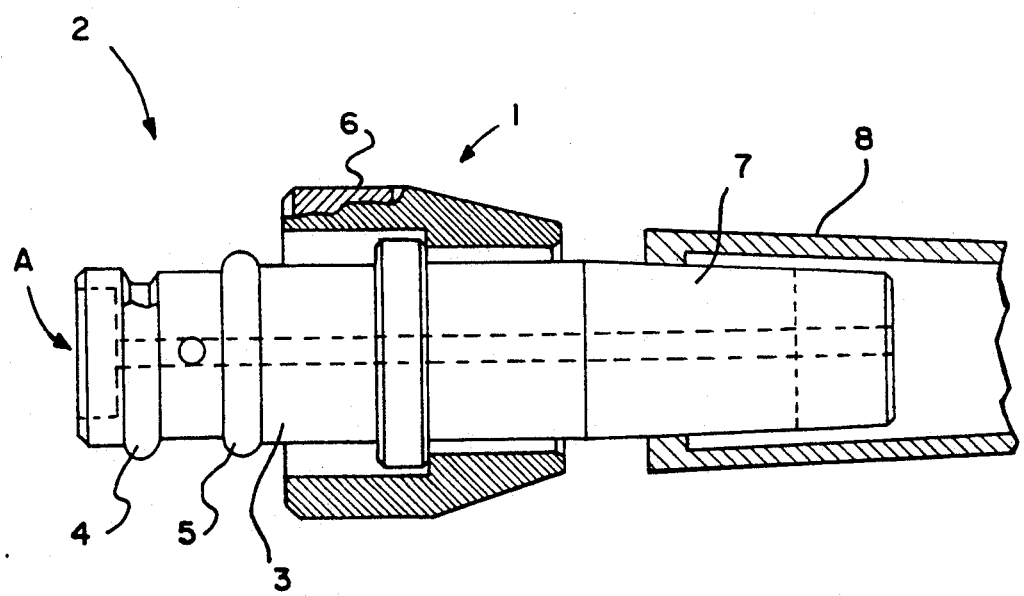
FIG. 1 is a longitudinal cross-sectional view of a dental syringe nozzle produced in accordance with the present invention.

FIG. 1 shows a syringe nozzle 1 which, through an adapter 2, can be interconnected with the body of a dental syringe (not shown). The adapter 2 is traversed lengthwise by bores A which permit the passage of rinsing water and drying air.

The proximal end of the body 3 of the nozzle 1 includes two grooves for receiving toroidal joints 4, 5 which serve to achieve a seal when attached to the end of a syringe body. A coupling ring 6 serves to lock the assembly in position (by a screw or ratchet connection). The distal end of the body 3 of the nozzle 1 includes a male cone 7 for receiving a disposable tube 8. To facilitate this, the male cone 7 preferably exhibits a taper of about 8%.

Figure 2:
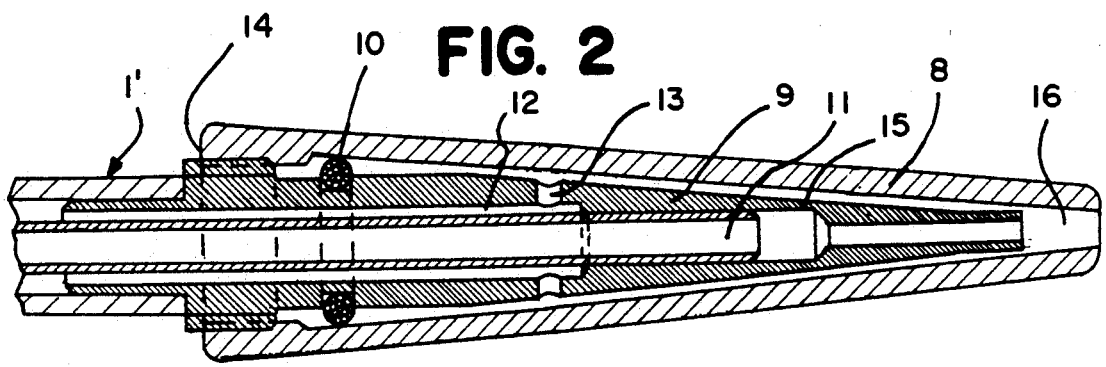
FIG. 2 is a longitudinal cross-sectional view of an alternative embodiment nozzle for a dental syringe.

The tube 8 is generally formed of a synthetic material, for example, PVC or polyethylene. Connection of the tube 8 can be achieved by a force fit with the male cone 7 of the syringe nozzle 1 of FIG. 1, or by a self-tapping arrangement with the end 9 of the syringe nozzle 1' of FIG. 2. To this end, the nozzle 1' of FIG. 2 is provided with a threaded portion 14 positioned upstream (or downstream) from a toroidal sealing joint 10.

As a consequence, water will be delivered through a longitudinal passage 11, for discharge at the end 16 of the nozzle 1', while air will be delivered through a longitudinal passage 12, passing through transverse bores 13 and between the outer face of the end 9 of the nozzle 1' and the inner face or the tube 8, for discharge at the end 16 of the nozzle 1'. Preferably, the transverse bores 13 each extend along the outer face of the end 9, forming a longitudinal flange in the end 9 of the nozzle 1'.

The passage 11 can be formed, for example, by flexible synthetic materials positioned on the inside of the passage 12. Such materials are then attached (e.g., by gluing) to the taper 15 of the end 9. As a result, the ultimate mixture of air and water takes place downstream from the joint 10. This also prevents use of the nozzle 1' without the tube 8. In any event, the end 16 of the tube 8 is preferably slightly longer than the end 9 of the nozzle 1' (or the male cone 7 of the nozzle 1 of FIG. 1) to prevent the formation of a drop which could remain and thus infect the syringe nozzle.

From the foregoing, it will be clear that the body of the syringe nozzle can be straight or elbow shaped. Likewise, the tube can be provided with an internal thread, or with projections for a self-tapping screw fit. In a simplified version of the foregoing, the air and water can be discharged directly from the end of the syringe nozzle, in conventional manner. Alternatively, air can be introduced through the tube 12 (by a pipe) for discharge along one of the transverse bores 13 in order to obtain a more uniform air pressure.

I claim:

1. A nozzle for use with a dental syringe having a syringe body, for projecting air, water, and mixtures of air and water in dental surgery, in combination with a disposable tube for preventing microbial and viral contamination between patients detachably connected to and overlying the nozzle, the nozzle comprising an adapter having means at a proximal end for connection with the syringe body, and a male conical projection at a distal end for mechanically receiving the tube, a first longitudinal passage formed in the nozzle for discharging water from the nozzle, and a plurality of transverse bores formed in the nozzle for communicating with a second longitudinal passage and a space defined between the male conical projection and the tube, for discharging air from between the nozzle and the tube.

2. The nozzle of claim 1 wherein the nozzle includes two longitudinally extending bores, one for passage of the water and one for passage of the air, and wherein the adapter includes two grooves for receiving toroidal joints for sealing engagement with the syringe body and a coupling ring for interlocking assembly with the syringe body.

3. The nozzle of claim 1 wherein the tube engages the male conical projection by means of a form fit with the nozzle.

4. The nozzle of claim 1 wherein the tube engages the male conical projection by means of a self-tapping arrangement with the nozzle.

5. The nozzle of claim 4 wherein the male conical projection includes a threaded fitting spaced from a toroidal sealing joint associated with the male conical projection.

6. The nozzle of claim 1 wherein the bores continue along the outer face of the male conical projection as a longitudinal flange formed in the male conical projection for discharge at an end thereof.

7. The nozzle of claim 1 wherein the first longitudinal passage is formed of a flexible synthetic material, positioned within the second longitudinal passage and attached to the male conical projection.

8. The nozzle of claim 1 wherein the nozzle has a straight or elbow shaped end.

9. The nozzle of claim 1 wherein the tube includes an internal means for a self-tapping screw fitting.

10. The nozzle of claim 1 wherein the tube is slightly longer than the male conical projection at an end thereof.

* * * * *